United States Patent
Krishnaswamy et al.

(10) Patent No.: US 7,077,328 B2
(45) Date of Patent: *Jul. 18, 2006

(54) ANALYTE TEST INSTRUMENT SYSTEM INCLUDING DATA MANAGEMENT SYSTEM

(75) Inventors: Sarath Krishnaswamy, Chelmsford, MA (US); Patrick Guiney, Concord, MA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 668 days.

(21) Appl. No.: 09/363,728

(22) Filed: Jul. 29, 1999

(65) Prior Publication Data
US 2002/0060247 A1 May 23, 2002

(51) Int. Cl.
*G06K 7/10* (2006.01)
(52) U.S. Cl. .............................. 235/472.01; 235/462.45
(58) Field of Classification Search ........... 235/742.01, 235/438, 462.45, 462.47, 472.01; 600/300, 600/316, 319, 320, 322, 347
See application file for complete search history.

(56) References Cited

U.S. PATENT DOCUMENTS

| | | | |
|---|---|---|---|
| 4,510,383 A | | 4/1985 | Ruppender |
| 4,592,893 A | | 6/1986 | Poppe et al. |
| 4,850,009 A | * | 7/1989 | Zook et al. .................. 235/375 |
| 4,857,716 A | * | 8/1989 | Gombrich et al. .......... 128/903 |
| 5,019,974 A | * | 5/1991 | Beckers ....................... 600/316 |
| 5,052,943 A | * | 10/1991 | Davis .......................... 439/357 |
| 5,066,859 A | * | 11/1991 | Karkar et al. ............ 250/339.09 |
| 5,074,977 A | * | 12/1991 | Cheung et al. .............. 204/400 |
| 5,281,395 A | | 1/1994 | Markart et al. |
| 5,307,263 A | * | 4/1994 | Brown ......................... 128/904 |
| 5,324,925 A | * | 6/1994 | Koenck et al. .............. 235/472 |
| 5,366,609 A | * | 11/1994 | White et al. ................. 204/403 |
| 5,445,967 A | * | 8/1995 | Deuter .......................... 235/462 |
| 5,507,288 A | * | 4/1996 | Böcker et al. ............... 128/633 |
| 5,511,108 A | | 4/1996 | Severt et al. |
| 5,515,170 A | * | 5/1996 | Matzinger et al. ........... 356/244 |
| 5,526,120 A | * | 6/1996 | Jina et al. ..................... 356/244 |
| 5,602,456 A | | 2/1997 | Cargin, Jr. et al. |

(Continued)

FOREIGN PATENT DOCUMENTS

DE 43 15 532 11/1993

(Continued)

OTHER PUBLICATIONS

"Satellite G", Publication No. 483787, May 1991, 10 pages.

(Continued)

*Primary Examiner*—Uyen-Chau N. Le
(74) *Attorney, Agent, or Firm*—David L. Weinstein

(57) ABSTRACT

A method of managing data for a plurality of analyte test instruments connected to a data communication network. The method comprises the steps of: detecting via a host computer the connection of each instrument to the data communication network; uploading data received from each instrument to the host computer; processing the uploaded data on the host computer for operator review; and downloading configuration data from the host computer to each test instrument, the downloaded data comprising instrument-specific setup and control data. The invention further involves a hand-held analyte test instrument and a docking station for the test instrument.

5 Claims, 16 Drawing Sheets

U.S. PATENT DOCUMENTS

| | | | |
|---|---|---|---|
| 5,628,890 A | 5/1997 | Carter et al. | |
| 5,637,856 A | 6/1997 | Bridgelall et al. | |
| 5,640,953 A * | 6/1997 | Bishop et al. | 128/630 |
| 5,657,201 A * | 8/1997 | Kochis | 235/472 |
| 5,714,123 A * | 2/1998 | Sohrab | 422/104 |
| 5,764,035 A * | 6/1998 | Lee | 320/160 |
| 5,805,416 A * | 9/1998 | Friend et al. | 235/472 |
| 5,805,807 A * | 9/1998 | Hanson et al. | 375/220 |
| 5,828,966 A * | 10/1998 | Davis et al. | 320/115 |
| 5,871,494 A * | 2/1999 | Simons et al. | 606/181 |
| 5,929,422 A | 7/1999 | Lappe | |
| 5,961,451 A * | 10/1999 | Reber et al. | 250/341.1 |
| 5,971,941 A * | 10/1999 | Simons et al. | 600/573 |
| 6,106,780 A * | 8/2000 | Douglas et al. | 422/58 |
| 6,295,506 B1 * | 9/2001 | Heinonen et al. | 600/301 |
| 6,830,731 B1 * | 12/2004 | Buechler et al. | 422/82.08 |

FOREIGN PATENT DOCUMENTS

| | | |
|---|---|---|
| EP | 0 251 520 | 1/1988 |
| EP | 0 290 683 | 11/1988 |
| EP | 0 387 630 | 9/1990 |
| EP | 0 405 513 | 1/1991 |
| EP | 0 684 575 | 11/1995 |
| EP | 0 796 588 | 9/1997 |
| EP | 0 796 590 | 9/1997 |
| EP | 0 833 140 | 4/1998 |
| JP | 07231574 A * | 8/1995 |
| WO | 94/11838 | 5/1994 |

OTHER PUBLICATIONS

Two Copies of The EPC Search Report.

* cited by examiner

SAMPLE OF DISPLAYED DATA

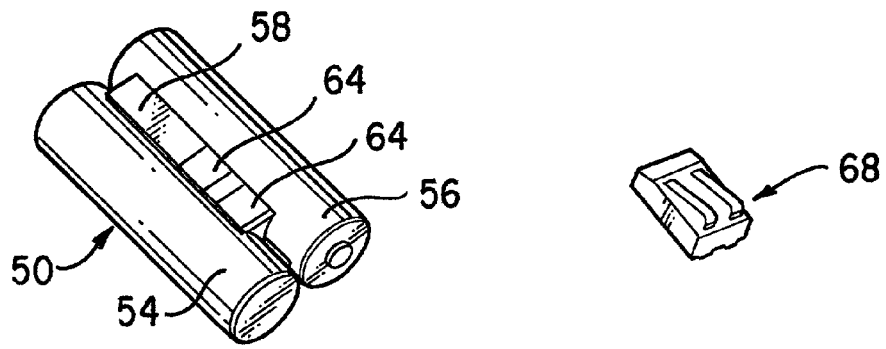
FIG. 8A
FIG. 8B
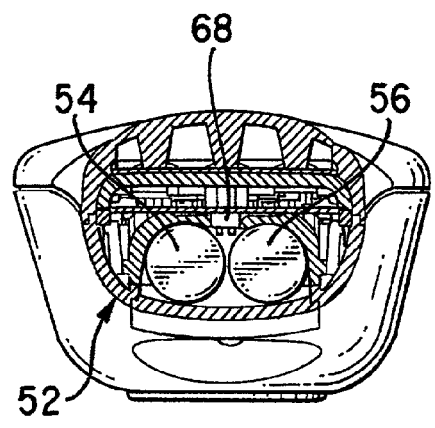
FIG. 9A
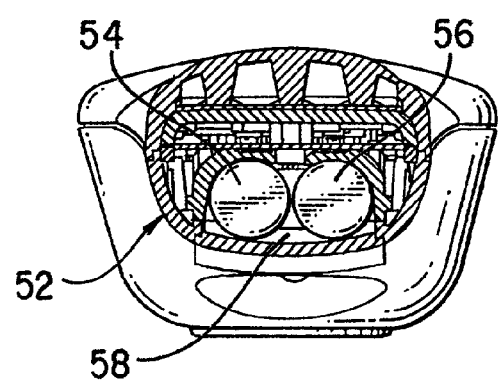
FIG. 9B

ANALYTE TEST INSTRUMENT SYSTEM INCLUDING DATA MANAGEMENT SYSTEM

BACKGROUND OF THE INVENTION

Health care professionals at medical institutions are routinely required to use various instruments to perform bedside tests on patients to monitor various aspects of patients' health. These tests generate substantial amounts of medical data which is often collected and organized for subsequent analysis. The data can include results of tests to determine the level of one or more analytes (e.g., blood glucose, ketones).

Traditionally, the primary means for collecting and organizing data obtained from the instruments is a printed or transcribed record of the test results. To review the results, a health care professional either retrieves the results from the institution's records department or goes to the patient's room. Since these results are often available only in printed form, chronological and statistical analysis is difficult.

Government regulations require medical institutions to perform control tests on instruments used for patient testing at regular intervals to ensure the accuracy of test results. Health care professionals that operate such instruments are also required to undergo periodic recertification.

Members of the institution's administrative staff are frequently responsible for the review of instrument control test data and recertification procedures to ensure compliance with federal regulations. In many instances, however, administrators identify tests involving "out-of-specification" instruments, expired supplies (e.g., test strips), or uncertified health care professionals after testing has been completed. These test results are either accepted or the patient can be subjected to another test.

It is therefore desirable to have a health data management system in which each of a plurality of medical test instruments are connected to a data communications network to provide real time transfer of patient test results to a centralized location. In addition, it is desirable to include in such a system a security mechanism for preventing testing of patients with "out-of-specification" instruments, expired supplies (e.g., test strips), or uncertified health care professionals.

SUMMARY OF THE INVENTION

A hand-held analyte test instrument has been developed. The instrument includes a barcode reader disposed in a housing for scanning a barcode associated with a test strip for receiving an analyte. The housing also includes a port for receiving the test strip. Electronic circuitry in electrical communication with the port is used for processing an analyte signal received from the test strip and generating analyte data. Also included is a display in electrical communication with the circuitry for displaying certain analyte data. The instrument also has a connector in electrical communication with the circuitry and connectable to a host computer over a data communications network. The circuitry automatically uploads analyte data to the host computer when the connector is connected to the network.

A hand-held analyte test instrument includes a housing having a port for receiving a test strip configured to receive an analyte. The instrument also includes electronic circuitry in electrical communication with the port and a connector. The electronic circuitry processes an analyte signal received from the test strip and generates analyte data. The connector is electrically connectable to a power source. The instrument also includes a display, a battery compartment, and a rechargeable battery pack. The display is in electrical communication with the circuitry and is used for display of certain analyte data. The battery compartment is formed in the housing and includes a pair of electrical contacts for providing power from a battery to the circuitry, and a pair of recharge contacts. The rechargeable battery pack is disposed in the battery compartment and includes a rechargeable battery disposed in a battery holder, and a bus bar disposed on the battery holder and in electrical communication with the recharge contact pair for recharging the battery when the instrument is connected to the power source.

A docking station for receiving a hand-held analyte test instrument has been developed. The docking station includes a connector, a switch, a first and second data port, and a control mechanism. The connector is electrically connectable to the instrument for receiving analyte test data. The switch is in electrical communication with the connector. The first data port and the second data port are in electrical communication with the switch. The first and second data ports are electrically connectable to a computer and a peripheral device, respectively. The control mechanism controls the switch to selectively pass the analyte data to the computer via the first data port or to the peripheral device via the second data port.

A method of managing data for a plurality of analyte test instruments connected to a data communication network includes the steps of detecting via a host computer the connection of each instrument to the network and uploading the data received from each instrument to the host computer. The method also includes the steps of processing the uploaded data on the host computer for operator review and downloading configuration data from the host computer to each instrument. The downloaded data includes setup and control data that can be specific to each instrument.

BRIEF DESCRIPTION OF THE DRAWINGS

The foregoing and other objects, features and advantages of the invention will become apparent from the following more particular description of preferred embodiments of the invention, as illustrated in the accompanying drawings. The drawings are not necessarily to scale, emphasis instead being placed on illustrating the principles of the present invention.

FIGS. 8A–8B are illustrations of a rechargeable battery pack and a two finger leaf spring contact connector for use with the rechargeable battery pack, respectively.

FIGS. 9A–9B are cross-sectional views of an analyte test instrument shown with alkaline power cells and with a rechargeable battery pack, respectively.

DETAILED DESCRIPTION

Figure 1:
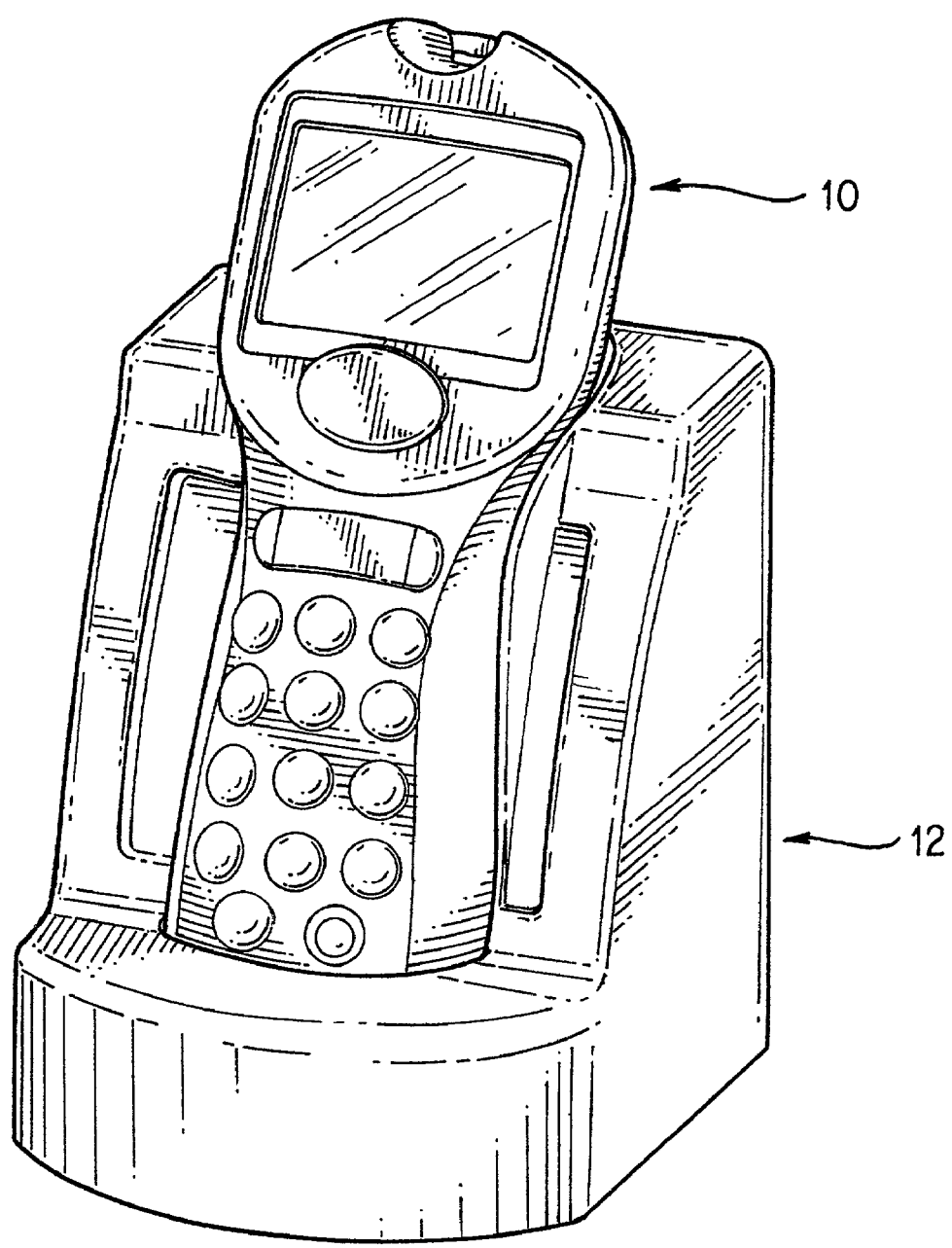
FIG. 1 is a perspective view of an analyte test instrument disposed in a docking station.

Referring to FIG. 1, an instrument 10 used in patient testing for one or more analytes (e.g., blood glucose, ketones, etc.) in a hospital environment is shown positioned in a docking station 12. The instrument 10 analyzes a patient sample (e.g., blood) deposited on one end of a test strip when the other end of the strip is inserted in the instrument 10. The docking station 12 allows for automatic transfer of test results to a host computer and provides power to recharge an internal battery pack when the instrument 10 is positioned in the station 12.

Figure 2:
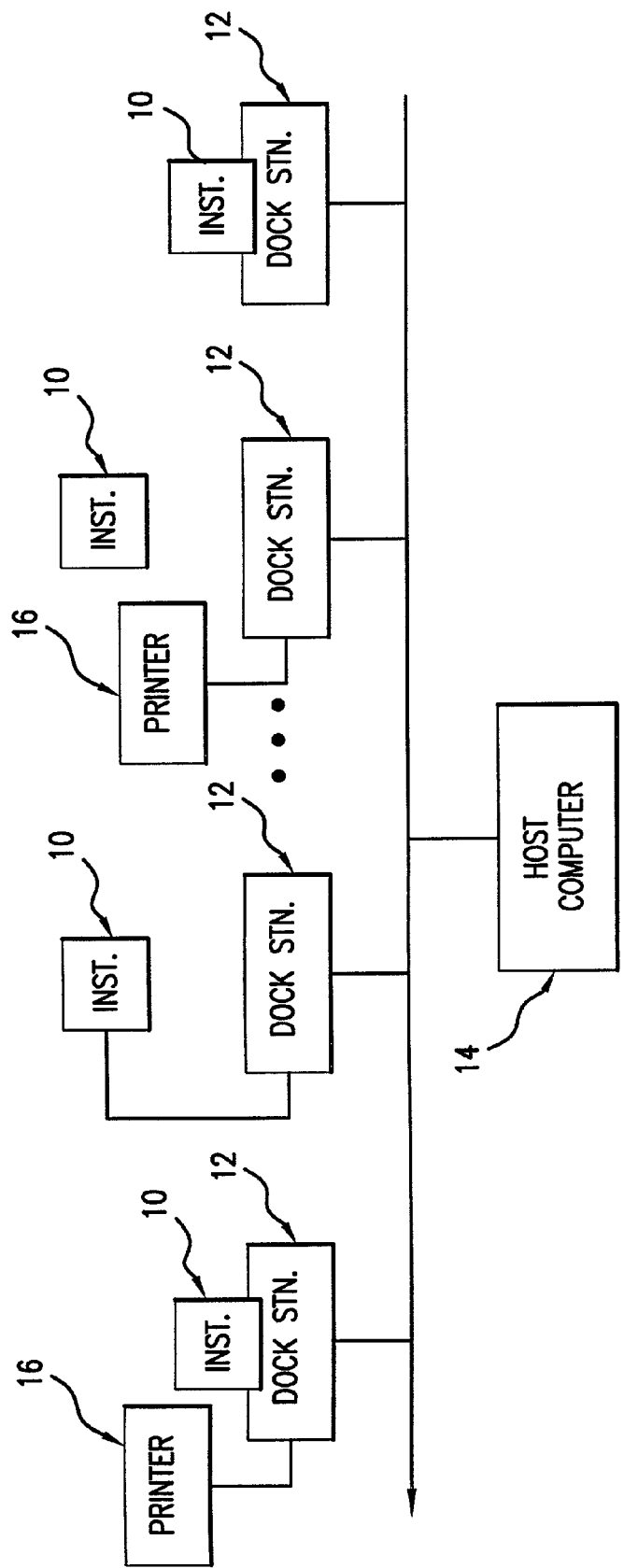
FIG. 2 is a functional block diagram of a plurality of medical test instruments connected to a host computer over a data communications network.

In a typical health care facility, a plurality of instruments 10 can be networked to a host computer 14 though docking stations 12 as shown in FIG. 2. For example, one instrument can be assigned to each patient room. A nurse or other operator inserts a test strip into the instrument and deposits a patient sample onto an exposed portion of the test strip. An audible indicator alerts the operator when a sufficient patient sample volume for analysis has been deposited on the test strip. The instrument then analyzes the sample and displays the results on the LCD module. The operator can return the instrument to the docking station 12, even before the results are available, where the test data (operator ID, patient ID, date, time, and other parameters) are automatically transferred via a cable to the host computer 14. The test data and results can be directed to a local printer 16 by a cable (e.g., an RS-232 standard interface cable) to generate a hardcopy, if desired. The network is controlled by the host computer 14 via a bi-directional data communication link, i.e., data can be transferred from the instrument 10 to the computer 14 and data can be transferred from the computer 14 to the instrument 10. The latter mode allows for remote independent configuration of individual instruments or groups of instruments.

Analyte Test Instrument

Figure 3A:
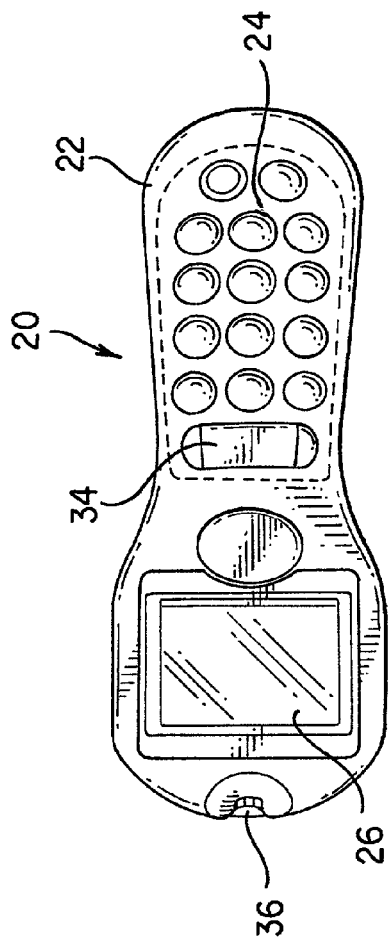
FIGS. 3A–3C are top, side and end views, respectively, of an analyte test instrument.
Figure 3B:
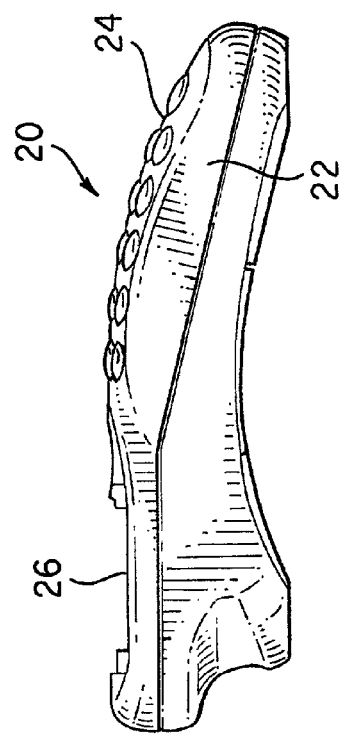
Figure 3C:
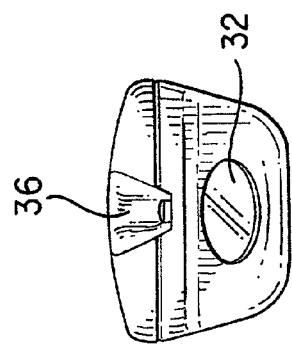
Figure 4:
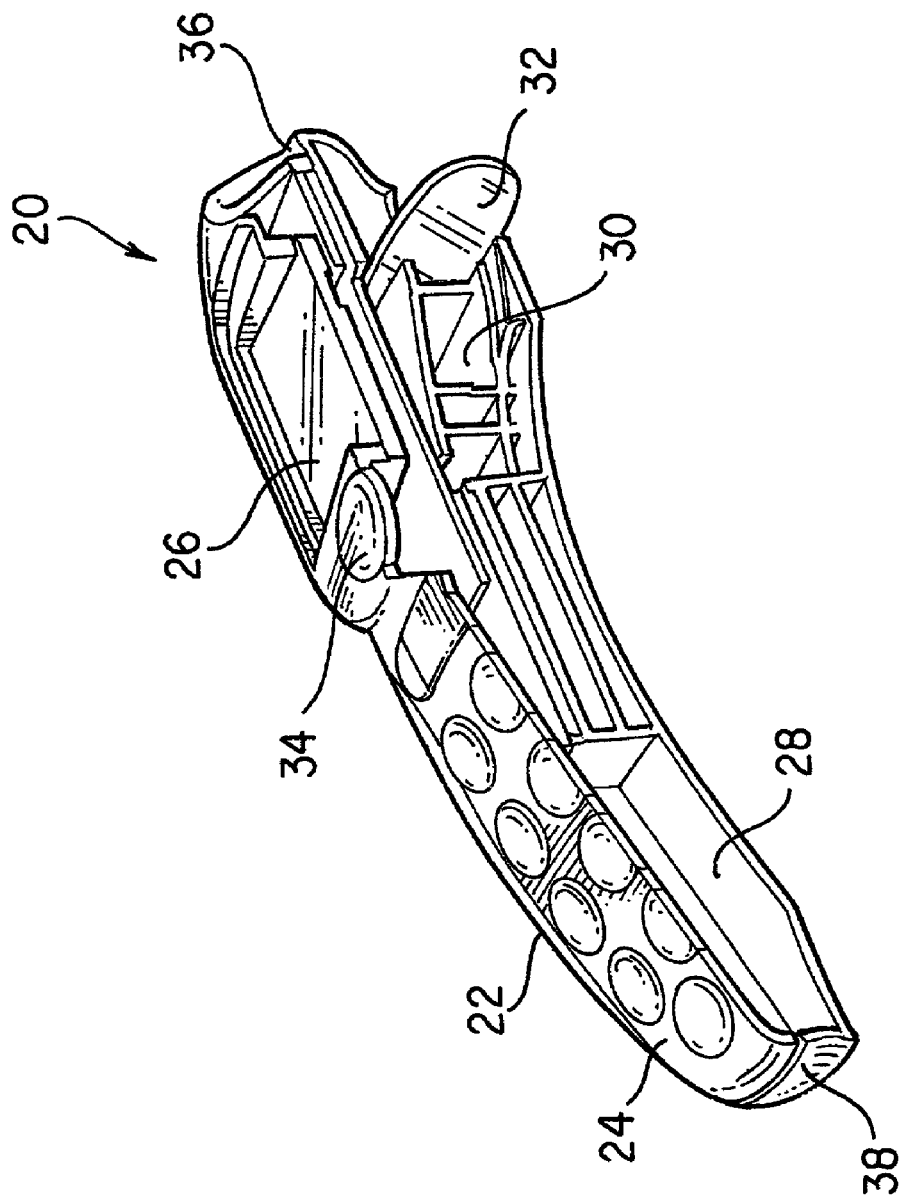
FIG. 4 is a cut-away perspective view of an analyte test instrument.

Referring to FIGS. 3 and 4, an analyte test instrument 20 includes a housing 22, a user interface 24, and a display area 26. The housing 22 is shaped to permit hand-held operation for bedside patient testing. The housing 22 includes an internal subframe 28 for mounting an analog and digital printed circuit boards and a barcode scan engine 30. The subframe also forms the battery cavity and includes battery contacts (not shown). The housing 22 is fabricated from rubber or plastic (e.g., ABS Polycarbonate). Smooth surfaces and a minimum of exposed fasteners and seams help to minimize areas which can collect foreign material and facilitates cleaning of the instrument. Silicone rubber pads are attached with adhesive to the bottom of the housing 22 to prevent skidding.

The user interface 24 includes a numeric keypad and function buttons to activate/deactivate power, select test or menu modes, edit entries, terminate entries, and activate a barcode reader as a substitute for manual numeric entry. All buttons in the user interface are fully sealed (e.g., using membrane switches). The keypad and barcode reader allow operators to enter a variety of data, including operator and patient identification (ID) numbers, strip control lot numbers, calibration codes, and to set other instrument parameters (e.g., date time, security intervals, display backlighting). The barcode reader is preferred for entry of test strip calibration data because it eliminates the need to visually verify a test strip code during each test.

Figure 5:
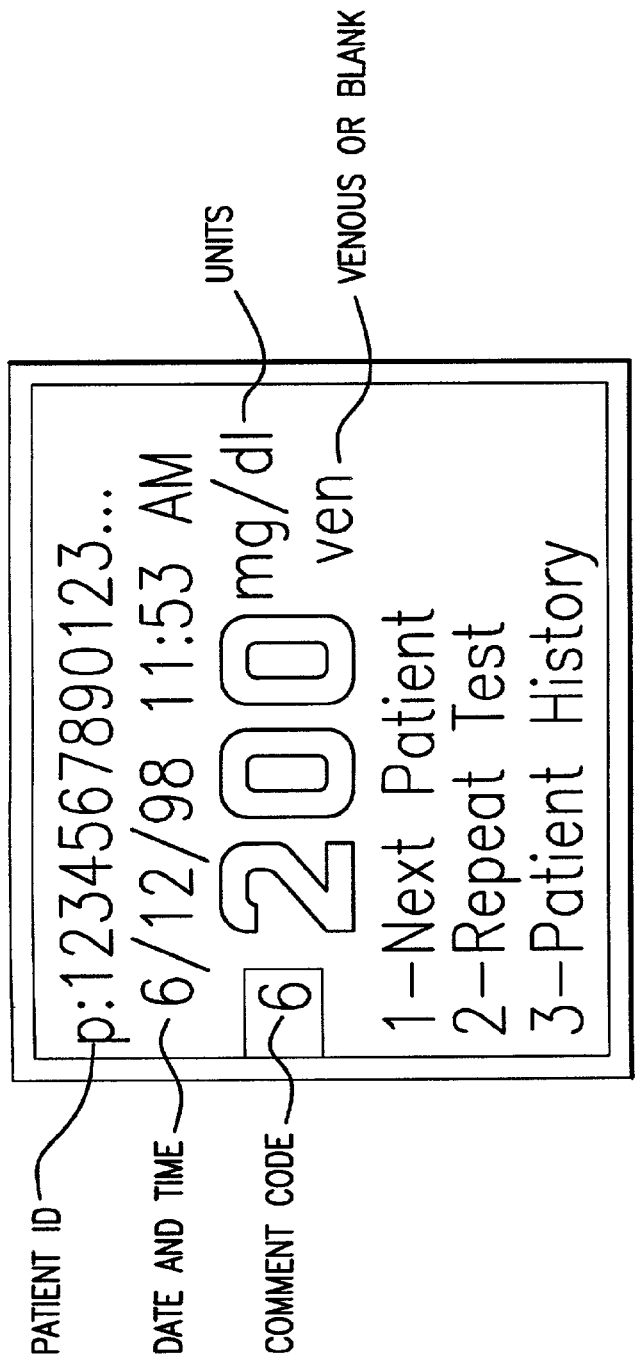
FIG. 5 is a sample of displayed data provided on a LCD module of an analyte test instrument.

The display 26 is a graphic style liquid crystal display (LCD) module and provides multiple lines of text characters. Referring to FIG. 5, a variety of prompts, audio and visual warnings, and menu items can be displayed along with numerical test results. The display 26 includes a selectable backlight mode utilizing four amber high intensity LED's to improve visibility in poor lighting conditions.

Referring back to FIGS. 3 and 4, the barcode reader comprises a laser scan engine 30 and a red acrylic exit window 32. The red exit window 32 acts as an optical filter to reduce the received light that is not matched to the wavelength of the scan engine laser source (e.g., 680 nm). The barcode reader includes optics disposed at the top of the hand-held instrument to provide non-contact reading of barcodes. The reader is activated by depressing the scan key 34 located at the top of the keypad. The barcode reader can only be activated if the operator is prompted for entry of any one of the following: operator ID, patient ID, or strip lot or control vial information. Identification can be entered manually or read into the instrument via the reader from barcoded identification tags (e.g., wristbands) worn by operators and patients. Barcoded items placed within several inches of the exit window 32 can be scanned after depressing the scan button 34 in the user interface 24. An audible signal indicates successful reading of the barcode.

Barcode readers are well-known in the art (e.g., retail checkout scanners) and are commercially sold by Symbol Technologies, Inc. U.S. Pat. No. 5,637,856, which is incorporated herein by reference, describes barcode scanning systems suitable for integration into an analyte instrument.

The instrument 20 includes a test strip port 36 which accepts test strips for determining the level of analyte in a sample taken from the patient. U.S. Pat. No. 5,628,890, which is incorporated herein by reference, shows one type of test strip.

A data port ten pin connector 38 is provided in the base of the instrument to allow connection with mating contacts in the docking station for data transfer, battery recharge (from external power source), and printer communication. The connector does not extend beyond the contour of the base end of the instrument. A single row of electrical contacts within the connector is recessed to prevent inadvertent contact with external conductors. The instrument 20 responds to commands uploaded from the host computer linked through the data port. The external computer system initiates data transfer without any action on the part of the operator after the instrument has been mated to the docking station.

Figure 6:
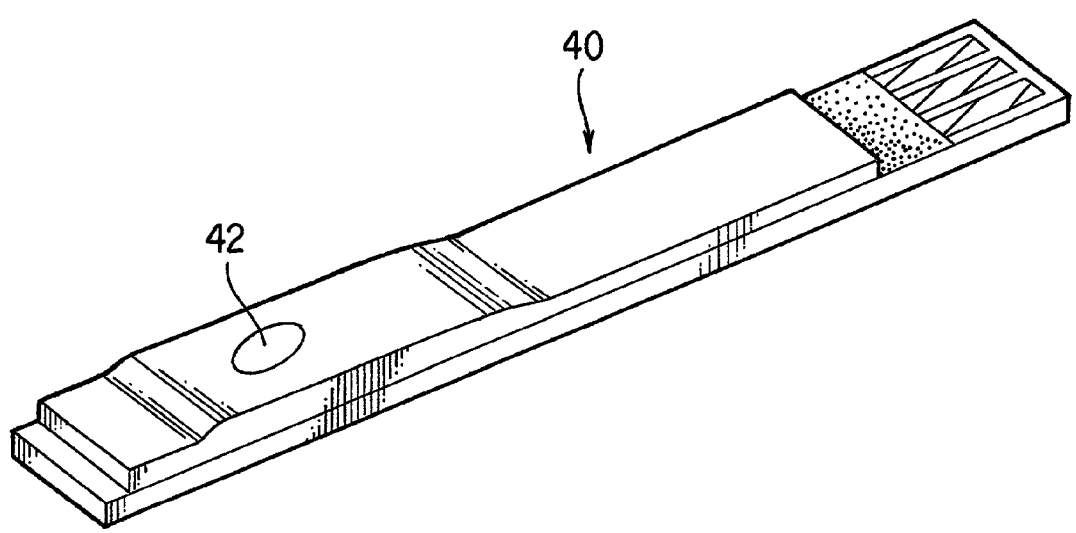
FIG. 6 is a perspective view of a three-electrode test strip for use with an analyte test instrument.

FIG. 6 shows one type of test strip 40 which includes three electrodes and can be used with the instrument (see FIG. 4) for determining the level of an analyte in the blood. The strip is partially inserted into the port 36 so that the sample area 42 remains outside the housing 22. The blood sample is applied to the sample area 42 and flows to an active area (not shown) at the unexposed ends of the three electrodes. The active area creates an electrochemical reaction in the sample, which is monitored electrically. Because each test strip typically has an expiration date, a strip identifier code which can be located on the strip package is either manually entered or scanned by the barcode reader into the instrument 20. If the strip code is not recognized as a valid code, then the instrument 20 alerts the operator and prevents further operation of the instrument 20 with that strip 40.

Figures 7A, 7B:
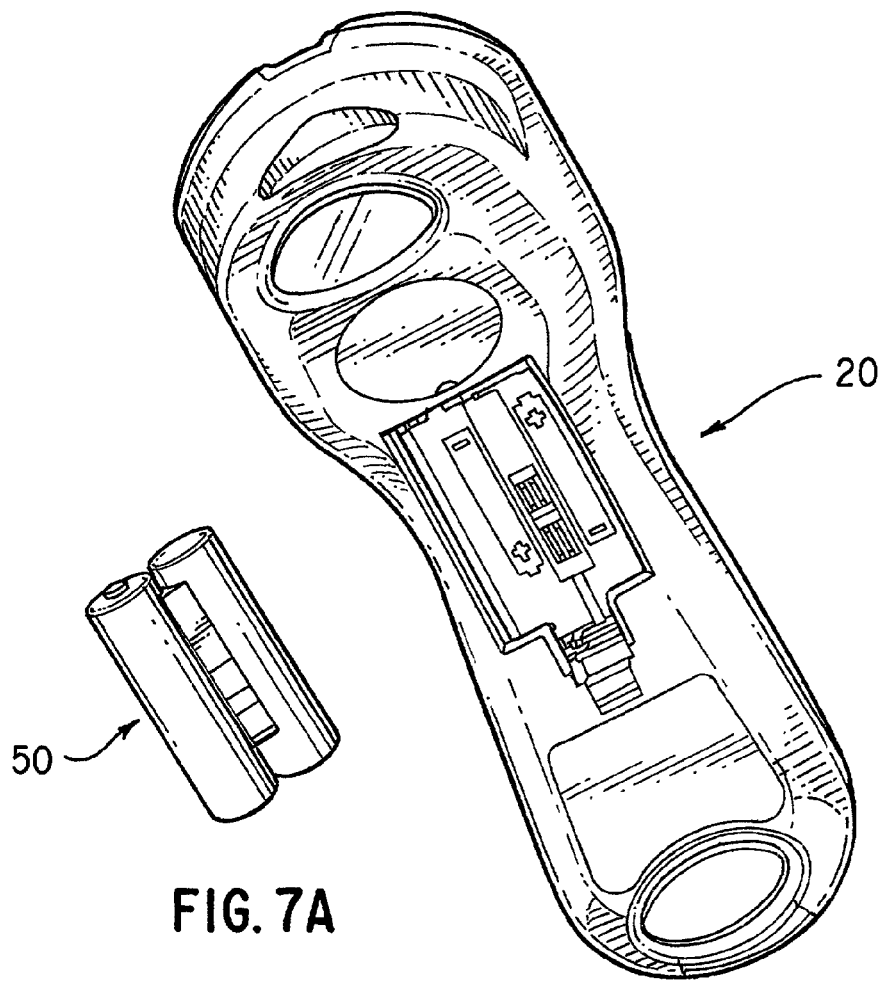
FIGS. 7 is a perspective view of the back of an analyte test instrument opened to expose a battery compartment and a separate rechargeable battery pack.

Referring to FIGS. 7 and 8A, the instrument 20 is powered by a rechargeable battery pack 50 (e.g., a nickel metal hydride (NiMH) battery package) securely disposed in a cavity 52 (i.e., battery compartment) on the underside of the instrument 20. The installed battery pack 50 (see FIG. 9A) is recharged by the docking station when the instrument is positioned in the docking station. Alternatively, the instrument can be powered by two standard alkaline batteries which are securely disposed in the same cavity 52 (see FIG. 9A). If an alkaline battery is installed improperly, it will not make electrical contact and the instrument will not turn on.

In addition, the possibility of inadvertently recharging the alkaline batteries is eliminated through the use of the custom-designed rechargeable battery pack 50. Also, keying features in the battery compartment are designed to prevent incorrect insertion of the battery pack or the insertion of a non-specified battery pack, thus eliminating the possibility of another battery chemistry from inadvertently being used.

Figure 10:
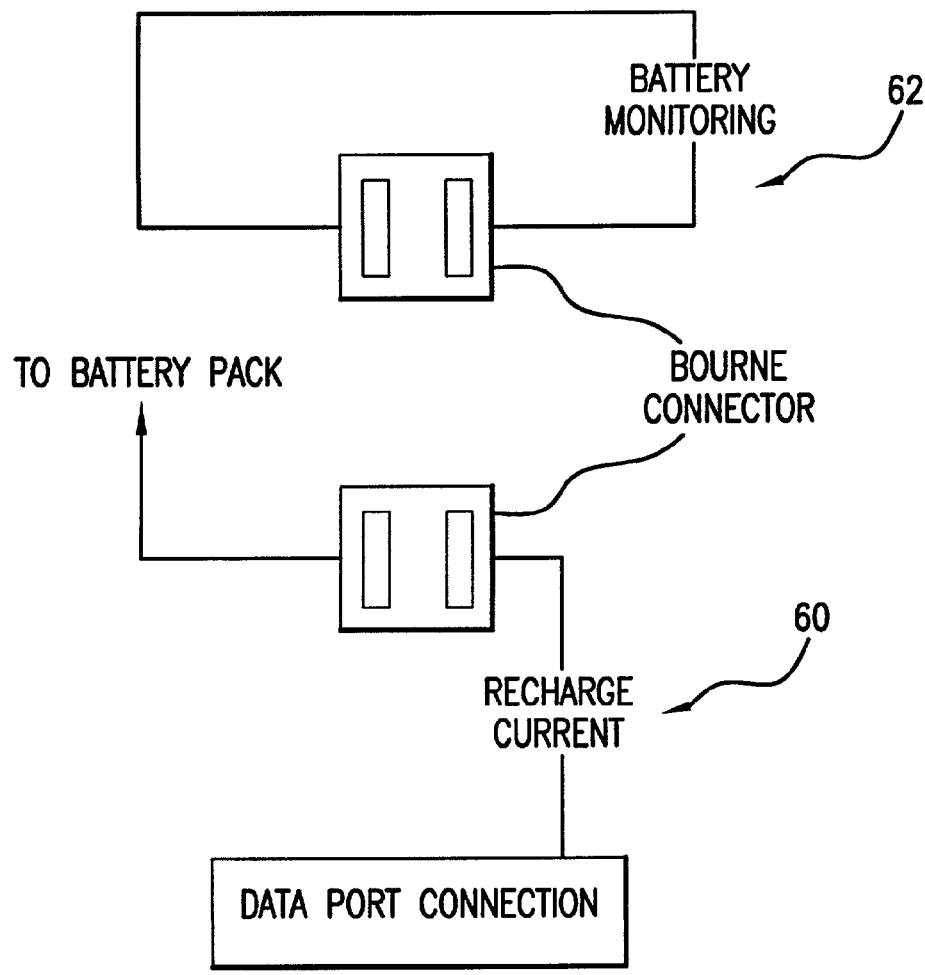
FIG. 10 is an illustration of a battery monitoring circuit and recharge current circuit employing a pair of two finger leaf spring contact connectors.

Referring to FIGS. 9A and 9B, the custom-designed battery pack 50 takes advantage of the void space that exists between two standard alkaline batteries 54, 56 when installed in the battery compartment 52, thereby eliminating the possibility of standard alkaline cells from activating the recharge functions. The recharge circuitry includes two independent circuits (see FIG. 10). The first circuit 60 provides recharge current to the rechargeable battery pack 50. The second circuit 62 determines the presence of the rechargeable battery pack 50 in order to facilitate the measuring of battery level. The pack 50 includes a plastic spine 58 which acts as a holder for the two NiMH batteries 54, 56 and occupies the void space which normally exists between two installed alkaline batteries. Referring back to FIG. 8A, two discrete conductive pads 64, 66 located in the plastic spine 58 act as bus bar contacts. Each bus bar contact is used in conjunction with a small two finger leaf spring contact connector 68 (e.g., Bourne connector) located within the void space in the battery compartment 52 (see FIGS. 8B and 9A–9B). Each finger is electrically independent of the other finger in the connector. When the battery pack 50 is installed, the two electrically discrete bus bar contacts in the plastic spine 58 create an electrical short across each of the two connectors, thereby completing two independent circuits (see FIG. 10). Because completion of the electrical paths requires electrical current to flow from one contact on the connector, through the bus bar contact, and out the other contact of the same connector, there is no possibility that recharge current can be supplied in any other battery system which does not utilize this battery pack configuration.

Docking Station

Figure 11A:
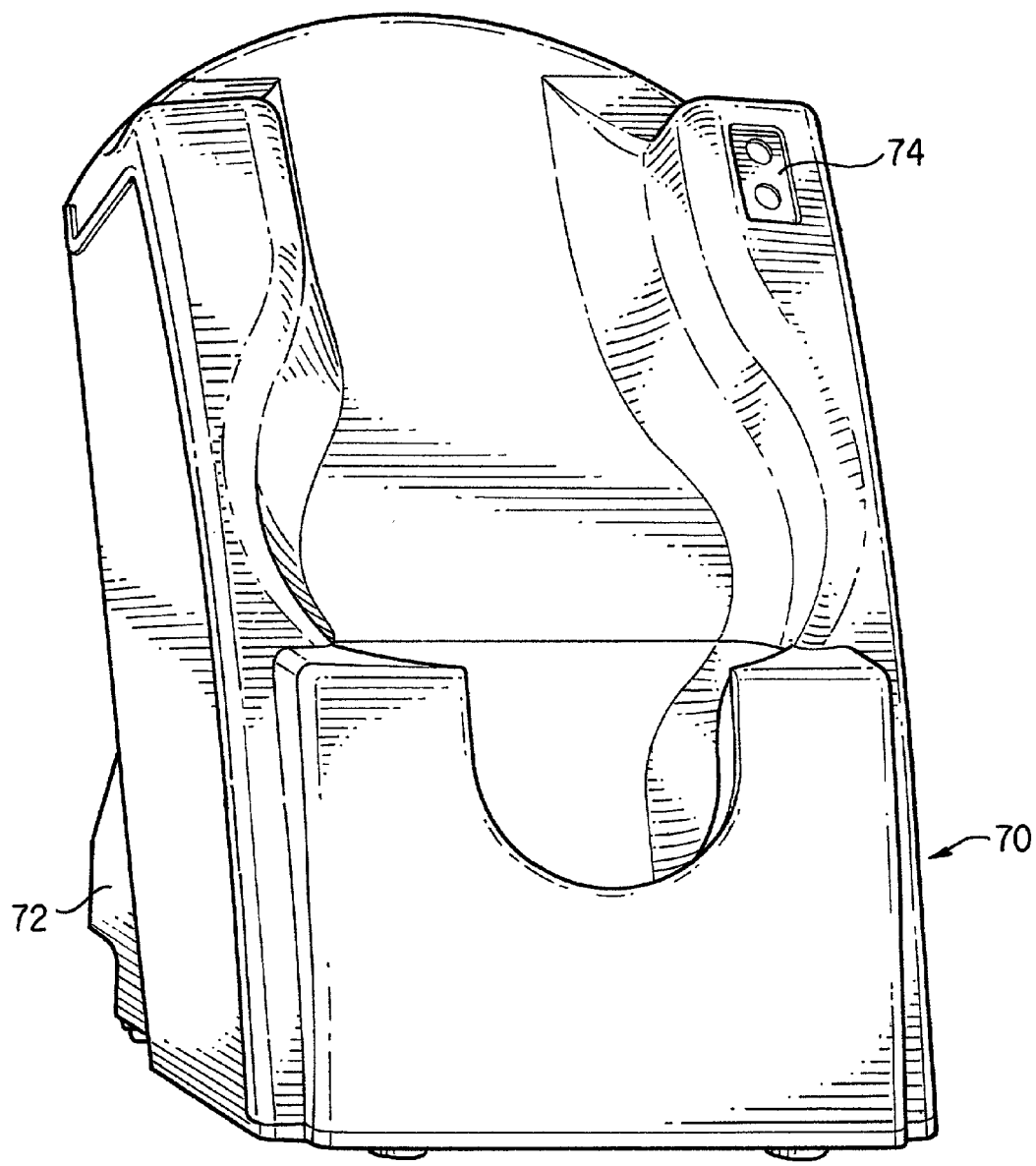
FIGS. 11A–11B is a perspective view of a docking station for use with an analyte test instrument.

FIG. 11A shows a docking station 70 in a desk mount configuration. An alternate wall mount configuration is achieved by repositioning an attached mounting bracket 72. The docking station 70 provides at least the following two important capabilities for the instrument. First, an instrument with a rechargeable battery pack is recharged when seated in the docking station. Second, data communication with the host computer or other devices can be established through the docking station. In particular, the docking station is capable of hands-free and near real-time transfer of (1) test data to a host computer and (2) configuration data from the host computer. The docking station 70 also serves as a convenient resting place for the instrument when not in use.

Figure 11B:
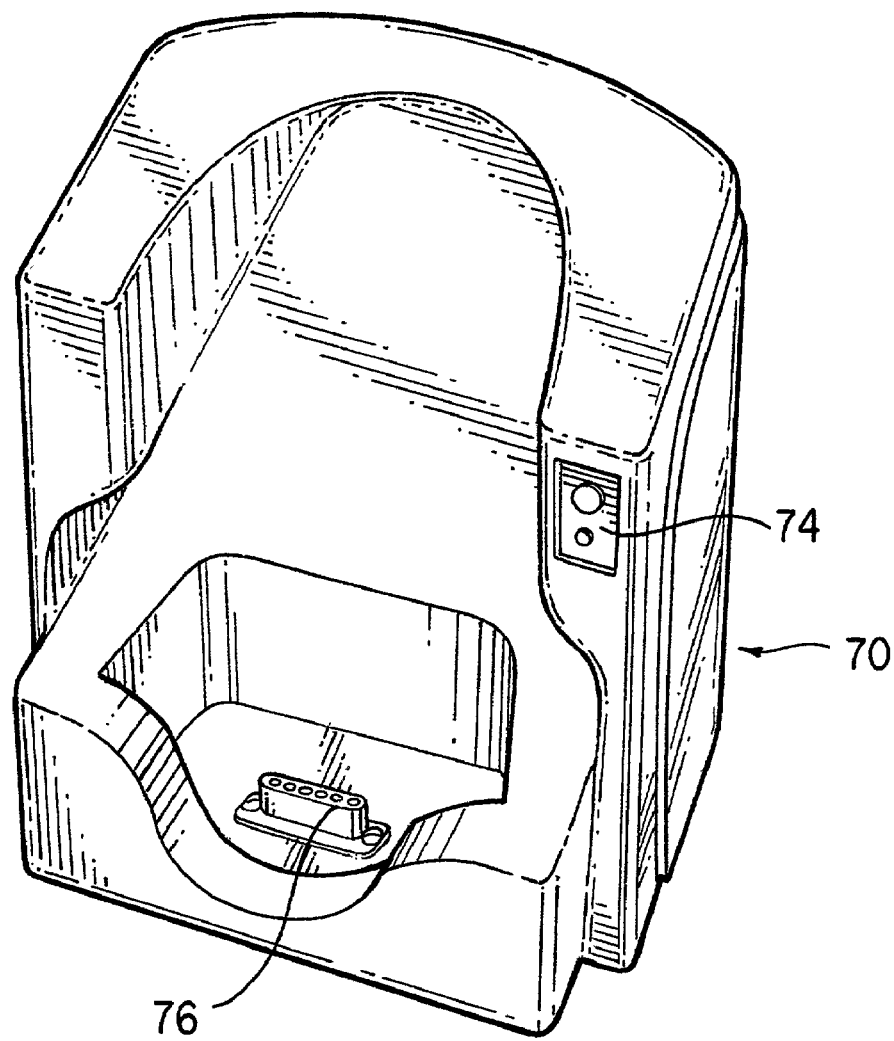

Power is provided to the docking station through an external AC adapter. Status lights 74 (e.g., LEDs) on the docking station indicate when power is on, when a meter has been docked successfully, and when data are being transferred through the docking station. The station 70 includes a docking connector 76 (see FIG. 11B) which includes a series of electrical contacts and is located in the recessed base. When the instrument is docked, the docking connector 76 receives a low insertion force (LIF) mated connector located in the base of the instrument. One of the station connector contacts provides power to the instrument for recharging the optional battery pack. The battery charge provided to the instrument is a low current (i.e., trickle charge) received from the docking station 70 through the instrument's data port connector 38. The docking station 70 incorporates circuitry to limit overcharging. Although the charging current is available at all times, only instruments equipped with a rechargeable battery pack are capable of receiving this current.

Figure 12:
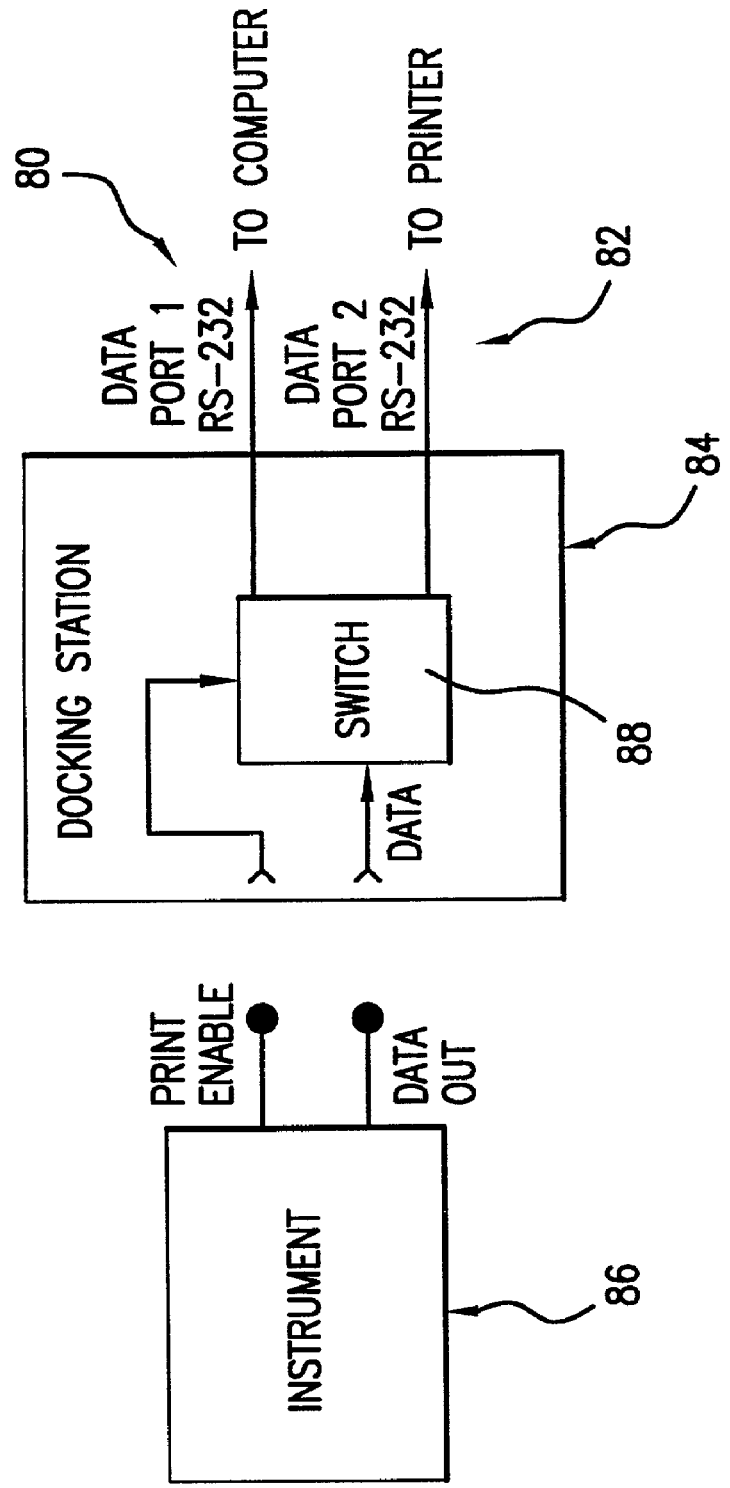
FIG. 12 is a functional block diagram of a docking station switching circuit for directing data transfer between two ports.

Referring to FIG. 12, the data connection through the docking station is essentially a pass-through connection from the instrument data port connector (see FIG. 4) to one of two standard 9-pin RS-232 ports. A first data port 80 is used for data transfer (e.g., to a computer, a modem, or an Ethernet terminal server) and the other port 82 is available for connection to a peripheral device (e.g., a printer). In its default condition, the docking station 84 is configured to pass data between the instrument 86 and the first data port 80. Data is passed to the second data port 82 when the docked instrument sets a switch 88 for the print mode. After data transfer through the second port 82 is completed, the docking station 84 resets switches to connect back to the first port 80.

The docking station 84 can be connected via a computer interface cable to a computer, a modem serial port, or some other communications port (e.g., Lantronix box) for data transfer over a communication line (e.g., a telephone or Ethernet TCP/IP line). The cable includes a standard nine pin RS-232 connector which mates with the docking station 84. A similar cable is used to communicate with a printer or other external device.

Figure 13:
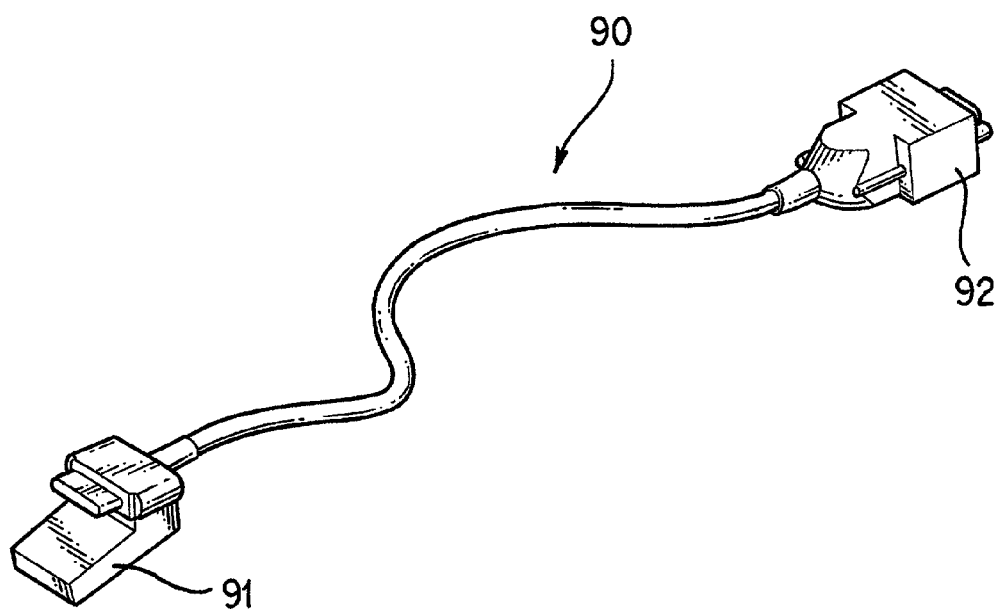
FIG. 13 is an illustration of a computer interface cable for use with a docking station.

FIG. 13 shows a different computer interface 90 cable which can be used in place of the docking station for direct communication with a computer (e.g., a laptop PC). The cable includes a standard DB9 connector 91 at one end and a RS-232 connector at the other end 92. This cable, however, does not include a means to recharge the battery pack.

Data Management System

A data management system facilitates the data communication and control between multiple instruments and a computer. The system is particularly advantageous to instruments used in a health care environment. The system allows test data to be automatically uploaded from each instrument to the host computer and subsequent reviewing, graphing and printing of the data. Uploaded data can be made available to other external systems through a specified port (i.e., a data forward port) for use in third party applications.

In addition, instrument configuration and security data can be downloaded to the individual instruments according to specific procedures or preferences.

Figure 14:
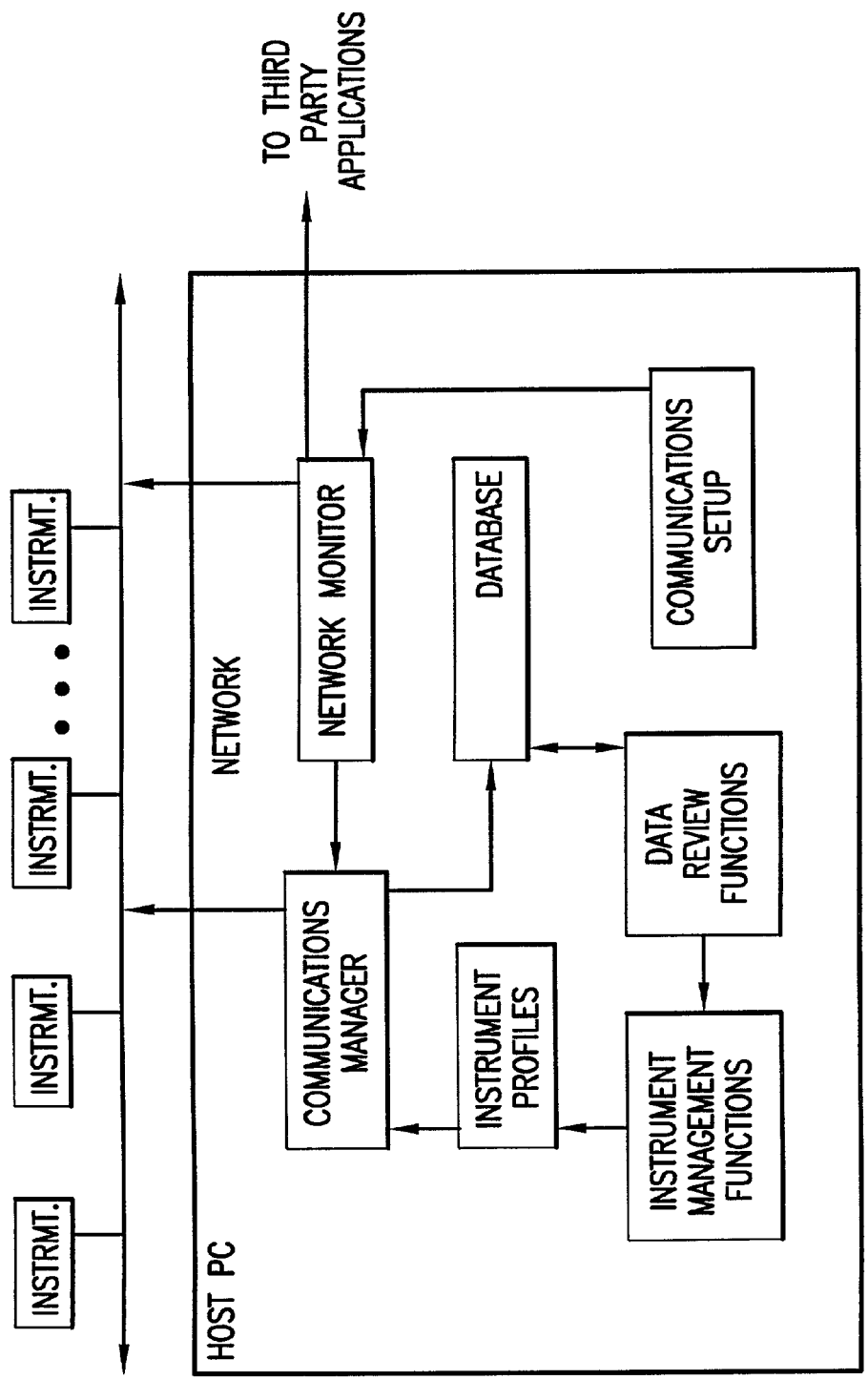
FIG. 14 is a functional block diagram of a data management system for use with multiple analyte test instruments in a hospital environment.
Figure 15A:
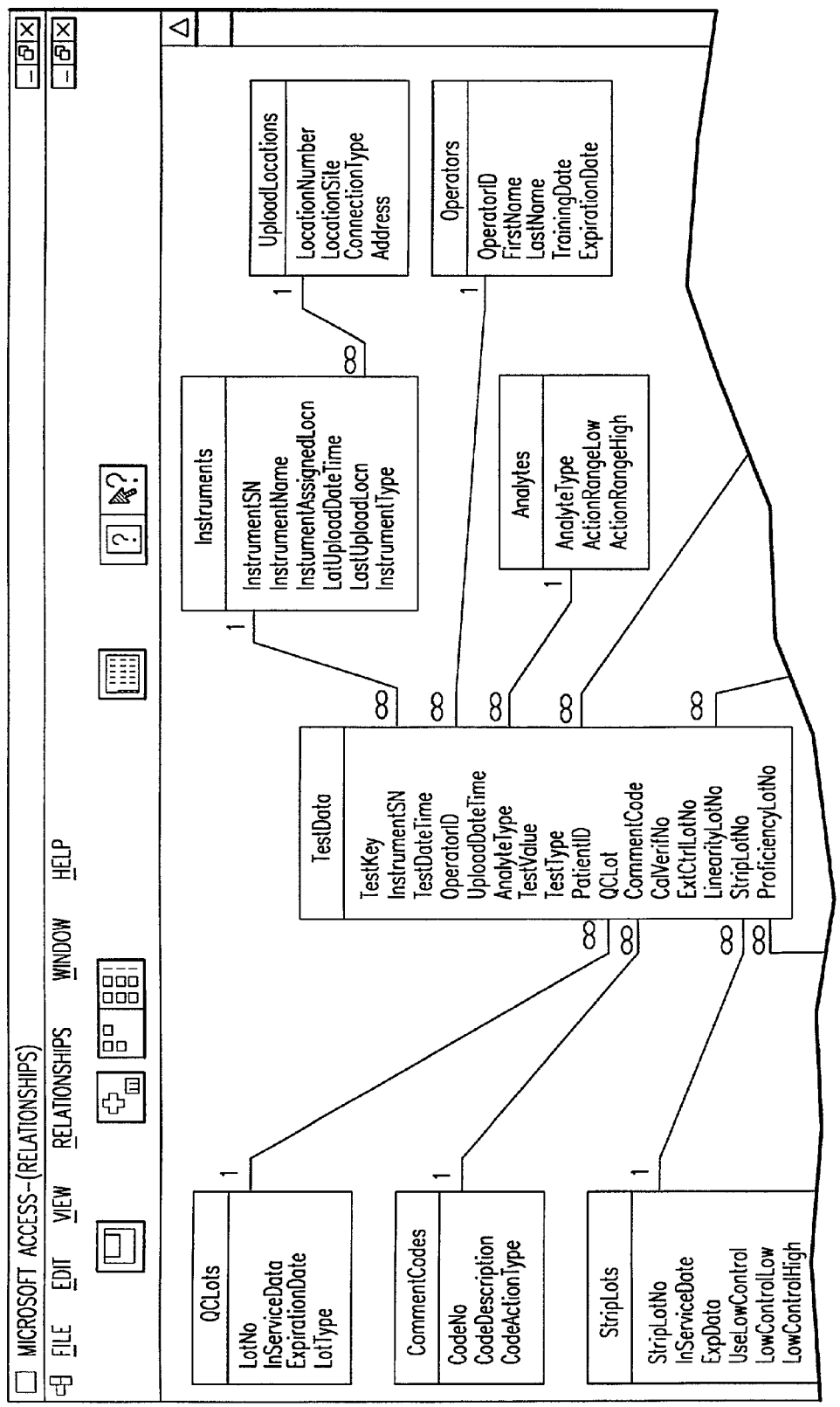
FIG. 15 shows one possible configuration of database tables for use in an analyte instrument data management system.
Figure 15B:
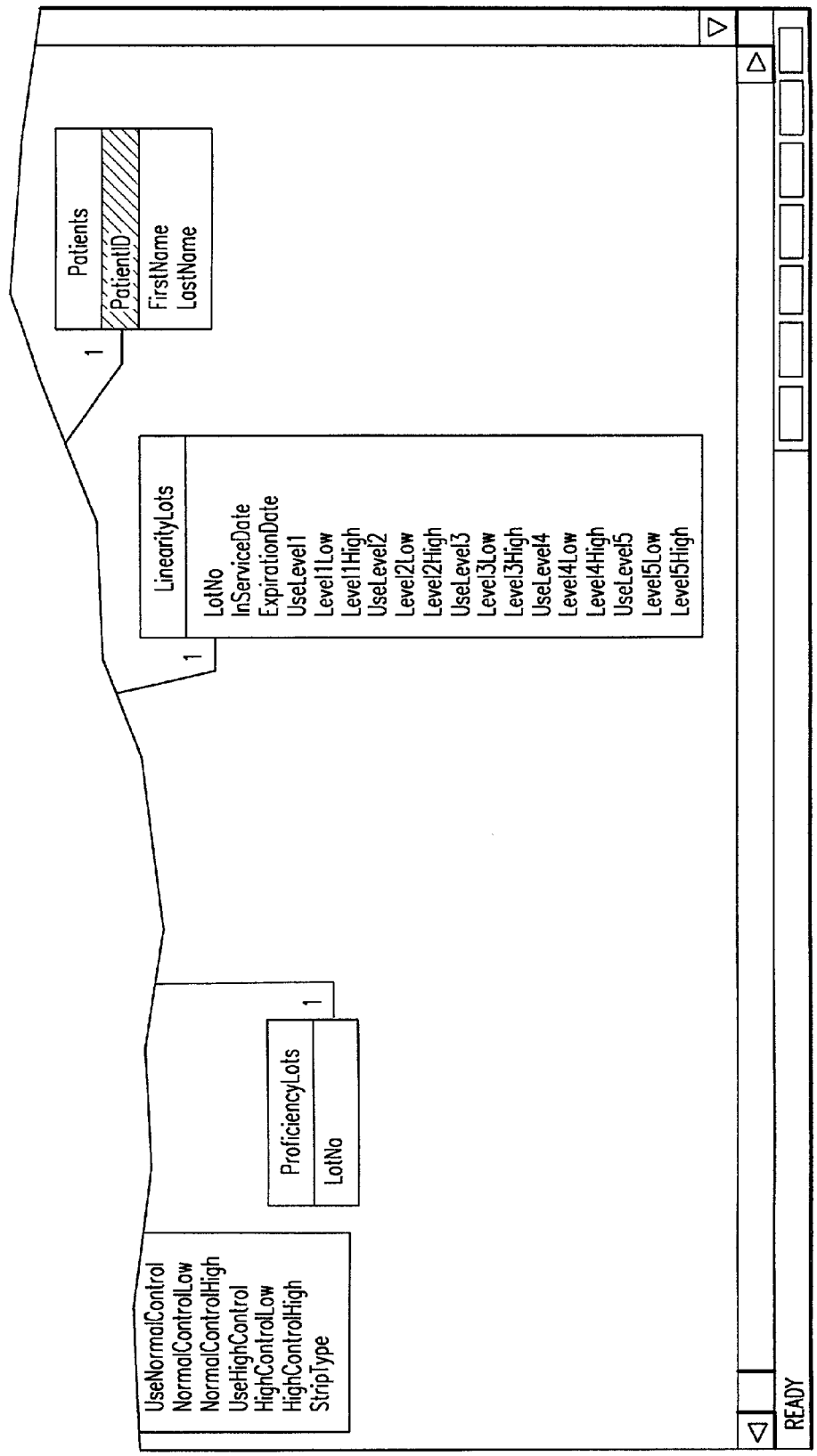

Referring to FIG. 14, a data management (DM) system is shown as a related group of functional blocks. When an instrument is placed in a docking station after testing, the instrument generates a message (i.e., signal) on the network indicating its presence. The host software monitors the network for messages transmitted from the instruments. When a message is received, the host acknowledges the message, determines the location of the docking station, and identifies the particular instrument. The host then reviews its database for instructions for that instrument and sends a set of instrument-specific data (e.g., commands to facilitate data transfer, calibration data) to the instrument before terminating the session. The specific data transferred are determined by the operator of the host computer in a previously executed setup operation. Data from the instruments are stored in a central database which is designed to be accessed by both the DM system and third party users (e.g., independent data applications).

Operators can interact with the DM system to configure upload and download procedures for transferring data to/from specific instruments or instrument groups. Operators can also use the DM system to review test data uploaded from instruments and stored in the database. In addition, operators can remotely monitor instruments and operator performance.

The network monitor function is a background process in the host software that monitors ports on the host computer to detect communication signals from the instruments. The network monitor can check selected TCP/IP ports, modem instruments, and computer serial ports. Once an instrument signal is detected, the network monitor promptly returns an acknowledgment signal to the instrument and determines its identification (i.e., serial number) and location. The network monitor forwards this information to the communications manager and then returns to monitoring the network for communications from other instruments. The network monitoring process can be initiated at the operator's option whenever (1) the host computer is booted, (2) the data review and instrument setup functions are started, or (3) the user specifically starts the network monitor executable. Once started, the network monitor runs continuously on the host unless specifically terminated by the operator. The operator can view the status of all instruments known to the DM system on a summary display screen that is continuously updated as instruments check in.

The communications manager is a set of functions within the host software for controlling data transfer between the host computer and the individual instruments. These functions allow connection to instruments in remote locations and facilitate automatic data transfer (i.e., without human intervention) to and from the instruments at all times. The communications manager opens a communications channel to the instrument and uploads information to the appropriate location in the database. It also downloads previously configured security and setup information to the instrument. Any or all of these functions are specified in advance by the operator using one or more of the instrument management functions. In the event that multiple instruments check in to the network simultaneously, multiple communications manager processes (i.e., one per instrument) can be implemented. Alternatively, a queue of instruments and corresponding network addresses can be established.

Instrument profiles are sets of commands for a group of instruments that are executed when the host computer establishes a connection to an instrument in that group. These commands are used to set the instrument configuration and security options (e.g., date, time, strip lot list, operator list). If there are no instructions for a given instrument, a default profile is used. Profiles are created by the instrument communications library functions which translate commands in the profiles according to the specific instrument type currently connected to the network.

An operator can use data review functions to access the database to view (numerically or graphically) or edit information. In some cases, these functions include data editing capabilities used for entering new data, including lists of operators or new quality control ranges, into the database. These functions also provide notifications or warnings based on a review of data uploaded from the instruments. Notifications can require a user response or acknowledgment for the item that triggered the warning. Warning items can include expired test strip lots, expired QC lots, unqualified operator or any other significant condition. Because these functions include modification of the main database, security procedures (e.g., password protection) are employed to prevent unauthorized modifications. Preferably, any modifications to the database are logged by independent software in an independent log file. Data review functions also permit a broad range of report generation and manipulation. Reports can include data listings, graphs and statistical information. File management functions allow the user to save, print, or otherwise manage the data files.

The instrument management functions are used to configure data to be sent to an instrument in the hospital. A point-and-click graphical user interface is used to select parameter setting for instrument upload and download, and to create data lists to be downloaded. The user interface includes instrument-specific dialogs that allow the user to configure setup items (i.e., parameters that affect instrument performance that are not directly related to the test). For example, the user interface includes a means for the user to review a list of operators in the database and to select a subset of these operators to download to an instrument. Similarly, a list of acceptable strip lots can be downloaded to each instrument. The download data are in the form of an instrument profile which can be activated at a later time when the instrument next connects in to the network (i.e., is returned to a docking station). An instrument grouping utility allows the user to create, modify and name groups of instruments within the hospital. All instruments within a given group share the same profile. Instrument setup functions are used to establish instrument settings and how the instrument performs its tests. Instrument security functions utilize operator and test strip lot lists stored in the database to establish which operators or test strips can be used with a given instrument.

The database used in the DM system is a standard commercially-available database (e.g., Access™, Oracle™) to allow access by other systems or devices. One possible configuration of database tables is shown in FIG. 14. The database stores test records from each device and can include parameters such as analyte type (e.g., glucose, ketones), test type (e.g., patient, control, etc.), operator ID (i.e., name, training date and/or expiration date), time and date of test, time and date of upload, strip lot data (e.g., QC ranges, service and/or expiration dates), patient ID, control lot ID, instrument name and assigned location, location of upload, pass/fail indication, and comment codes (including text descriptions of numeric comment codes).

What is claimed is:

1. A hand-held analyte test instrument comprising:
a housing;
a barcode reader disposed in the housing for scanning a barcode associated with a test strip configured to receive an analyte;
a user interface for activating said barcode reader, said user interface further comprising a numeric keypad and function buttons, said numeric keypad and function buttons for carrying out the functions of activating/deactivating power, selecting test or menu modes, editing entries, terminating entries, and activating said barcode reader as a substitute for manual numeric entry;
a port disposed in the housing for receiving the test strip;
electronic circuitry in electrical communication with the port for processing an analyte signal received from the test strip and generating analyte data therefrom;
a display in electrical communication with the circuitry for displaying certain analyte data; and
a connector in electrical communication with the circuitry and electrically connectable to a host computer via a data communications network, wherein the circuitry automatically uploads the analyte data to the host computer upon connection thereto.

2. The instrument of claim 1, wherein said user interface is further allowing an operator to enter data.

3. A hand-held analyte test instrument comprising:
a housing;
a port disposed in the housing for receiving a test strip configured to receive an analyte;
a barcode reader disposed in the housing for scanning a barcode associated with a test strip configured to receive an analyte;
a user interface for allowing an operator to enter data, said user interface comprising a numeric keypad and function buttons, said numeric keypad and function buttons for carrying out the functions of activating/deactivating power, selecting test or menu modes, editing entries, terminating entries, and activating a barcode reader as a substitute for manual numeric entry;
electronic circuitry in electrical communication with the port for processing an analyte signal received from the test strip and generating analyte data therefrom;
a display in electrical communication with the circuitry for displaying certain analyte data;
a connector in electrical communication with the circuitry and electrically connectable to a power source;
a battery compartment formed in the housing and comprising a pair of electrical contacts for providing power from a battery to the electronic circuitry and a pair of recharge contacts; and
a rechargeable battery pack disposed in the battery compartment and comprising (1) a rechargeable battery and (2) a battery holder in which the rechargeable battery is disposed, a bus bar disposed on the battery holder and in electrical communication with the pair of recharge contacts for recharging the battery when the instrument is connected to the power source.

4. The instrument of claim 3, wherein said barcode reader is activated by said user interface.

5. A docking station for receiving a hand-held analyte test instrument, the docking station comprising:
a connector electrically connectable to the instrument for receiving analyte data therefrom;
a switch in electrical communication with the connector;
a first data port in electrical communication with the switch and being electrically connectable to a computer;
a second data port in electrical communication with the switch and being electrically connectable to a peripheral device; and
a control mechanism for controlling the switch to selectively pass the analyte data to the computer via the first data port or to the peripheral device via the second data port; said docking station being configured to pass data between said analyte test instrument and said first data port when said docking station is in a default condition, and
circuitry to prevent overcharging.

* * * * *

UNITED STATES PATENT AND TRADEMARK OFFICE
CERTIFICATE OF CORRECTION

PATENT NO.         : 7,077,328 B2                                          Page 1 of 1
APPLICATION NO.    : 09/363728
DATED              : July 18, 2006
INVENTOR(S)        : Sarath Krishnaswamy It is certified that error appears in the above-identified patent and that said Letters Patent is hereby corrected as shown below:

Title Page

Please add:

Related U.S. Application Data

Provisional application No. 60/094,895, filed on Jul. 31, 1998.

Signed and Sealed this

Fifteenth Day of June, 2010

David J. Kappos
*Director of the United States Patent and Trademark Office*